(12) United States Patent
Dianna et al.

(10) Patent No.: US 6,195,119 B1
(45) Date of Patent: *Feb. 27, 2001

(54) DIGITALLY MEASURING SCOPES USING A HIGH RESOLUTION ENCODER

(75) Inventors: Andreas E. Dianna, Walnut Port, PA (US); James G. Costello, Huntington, NY (US)

(73) Assignee: Olympus America, Inc., Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/004,264

(22) Filed: Jan. 8, 1998

Related U.S. Application Data

(63) Continuation of application No. 08/502,984, filed on Jul. 17, 1995, now Pat. No. 5,801,762, which is a continuation-in-part of application No. 08/365,636, filed on Dec. 28, 1994, now Pat. No. 5,573,492.

(51) Int. Cl.[7] .................................................. H04N 7/18
(52) U.S. Cl. ............................................................ 348/65
(58) Field of Search ........................... 348/65, 348, 357; 385/117–118; 356/241; 359/367, 642; 607/1; 600/163, 167–168

(56) References Cited

U.S. PATENT DOCUMENTS

| | | | |
|---|---|---|---|
| 3,730,632 | * 5/1973 | Chikama ................................ 356/156 |
| 3,817,635 | * 6/1974 | Kawahara ............................. 356/171 |
| 3,819,267 | * 6/1974 | Kawahara ............................... 356/21 |
| 4,207,594 | * 6/1980 | Morris et al. ......................... 348/141 |
| 4,343,300 | * 8/1982 | Hattori .................................... 128/6 |
| 4,488,039 | * 12/1984 | Sato et al. ............................. 250/216 |
| 4,558,691 | * 12/1985 | Okada ...................................... 128/6 |
| 4,588,294 | * 5/1986 | Siegmund ............................. 356/241 |
| 4,702,229 | * 10/1987 | Zobel ...................................... 128/4 |
| 4,711,999 | * 12/1987 | Shishido et al. ...................... 250/204 |
| 4,737,622 | * 4/1988 | Shishido et al. ...................... 250/204 |
| 4,742,815 | * 5/1988 | Ninan et al. ............................. 128/4 |
| 4,783,701 | * 11/1988 | Ishida et al. ...................... 358/213.19 |
| 4,820,043 | * 4/1989 | Diener .................................. 356/241 |
| 4,844,071 | * 7/1989 | Chen et al. ............................... 128/6 |
| 4,905,668 | * 3/1990 | Ohsawa ................................... 128/6 |
| 4,980,763 | * 12/1990 | Lia ........................................ 348/67 |
| 5,045,936 | * 9/1991 | Lobb et al. ............................. 348/67 |
| 5,070,401 | * 12/1991 | Salvati et al. .......................... 348/65 |
| 5,214,538 | * 5/1993 | Lobb .................................... 359/691 |
| 5,313,306 | * 5/1994 | Kuban et al. ............................ 348/65 |
| 5,347,987 | * 9/1994 | Feldstein et al. ....................... 128/4 |
| 5,373,317 | * 12/1994 | Salvati et al. .......................... 348/65 |
| 5,455,649 | * 10/1995 | Yamada et al. .................... 354/195.1 |
| 5,573,492 | * 11/1996 | Dianna et al. ........................ 600/117 |
| 5,801,762 | * 9/1998 | Dianna et al. ......................... 348/65 |

FOREIGN PATENT DOCUMENTS 5-288998 * 11/1993 (JP) .

* cited by examiner

Primary Examiner—Vu Le
(74) Attorney, Agent, or Firm—Kenyon & Kenyon

(57) ABSTRACT

A system for determining a dimension of a detail including an optical scope for producing an image of the detail, an image scaling device for providing a scaled image size, and a processor. The system also includes a video camera which is either within the optical scope or external to the optical scope. The optical scope includes a focusing device for adjusting a focal position of the image of the detail and a device for providing a focus position signal based a position of the focusing device. If the system includes an external video camera, the optical scope also includes a viewer for passing the image of the detail to a plane outside of the optical scope. The video camera optically is coupled with the viewer of the optical scope or with the image of the detail and produces a video signal of the detail from the image of the detail. The processor converts the focus position signal into an object distance signal, or a magnification signal, or both, and determines the dimension of the detail based on the scaled image size and based on the object distance signal, or the magnification signal, or both.

7 Claims, 15 Drawing Sheets

Fig. 9a CHANNEL A
Fig. 9b CHANNEL B
Fig. 9c CHANNEL I

| Count | +0 | +5 | +10 | +15 | +20 | +25 | +30 | +35 | +40 | +45 |
|---|---|---|---|---|---|---|---|---|---|---|
| 900 | 668.7 | 632.7 | 599.0 | 567.5 | 538.0 | 510.3 | 484.4 | 460.1 | 437.3 | 415.9 |
| 950 | 395.8 | 376.8 | 359.0 | 342.3 | 326.5 | 311.6 | 297.5 | 284.3 | 271.8 | 259.9 |
| 1000 | 248.8 | 238.2 | 228.2 | 218.7 | 209.7 | 201.2 | 193.2 | 185.5 | 178.3 | 171.4 |
| 1050 | 164.8 | 158.6 | 152.7 | 147.0 | 141.7 | 136.5 | 131.7 | 127.0 | 122.6 | 118.4 |
| 1100 | 114.4 | 110.5 | 106.9 | 103.4 | 100.0 | 96.8 | 93.7 | 90.8 | 88.0 | 85.3 |
| 1150 | 82.7 | 80.2 | 77.9 | 75.6 | 73.4 | 71.3 | 69.3 | 67.4 | 65.5 | 63.8 |
| 1200 | 62.0 | 60.4 | 58.8 | 57.3 | 55.8 | 54.4 | 53.0 | 51.7 | 50.5 | 49.3 |
| 1250 | 48.1 | 46.9 | 45.9 | 44.8 | 43.8 | 42.8 | 41.9 | 40.9 | 40.1 | 39.2 |
| 1300 | 38.4 | 37.6 | 36.8 | 36.0 | 35.3 | 34.6 | 33.9 | 33.3 | 32.7 | 32.0 |
| 1350 | 31.4 | 30.9 | 30.3 | 29.8 | 29.2 | 28.7 | 28.2 | 27.7 | 27.3 | 26.8 |
| 1400 | 26.4 | 26.0 | 25.5 | 25.1 | 24.7 | 24.4 | 24.0 | 23.6 | 23.3 | 22.9 |
| 1450 | 22.6 | 22.3 | 22.0 | 21.7 | 21.4 | 21.1 | 20.8 | 20.6 | 20.3 | 20.0 |
| 1500 | 19.8 | 19.5 | 19.3 | 19.1 | 18.8 | 18.6 | 18.4 | 18.2 | 18.0 | 17.8 |
| 1550 | 17.6 | 17.4 | 17.2 | 17.1 | 16.9 | 16.7 | 16.5 | 16.4 | 16.2 | 16.1 |
| 1600 | 15.9 | 15.8 | 15.6 | 15.5 | 15.4 | 15.2 | 15.1 | 15.0 | 14.9 | 14.7 |
| 1650 | 14.6 | 14.5 | 14.4 | 14.3 | 14.2 | 14.1 | 14.0 | 13.9 | 13.8 | 13.7 |
| 1700 | 13.6 | 13.5 | 13.4 | 13.4 | 13.3 | 13.2 | 13.1 | 13.1 | 13.0 | 12.9 |
| 1750 | 12.8 | 12.8 | 12.7 | 12.6 | 12.6 | 12.5 | 12.5 | 12.4 | 12.4 | 12.3 |
| 1800 | 12.2 | 12.2 | 12.1 | 12.1 | 12.1 | 12.0 | 12.0 | 11.9 | 11.9 | 11.8 |
| 1850 | 11.8 | 11.8 | 11.7 | 11.7 | 11.7 | 11.6 | 11.6 | 11.6 | 11.5 | 11.5 |
| 1900 | 11.5 | 11.5 | 11.4 | 11.4 | 11.4 | 11.4 | 11.4 | 11.3 | 11.3 | 11.3 |
| 1950 | 11.3 | 11.3 | 11.3 | 11.2 | 11.2 | 11.2 | 11.2 | 11.2 | 11.2 | 11.2 |
| 2000 | 11.2 | 11.2 | 11.2 | 11.2 | 11.2 | 11.2 | 11.2 | 11.2 | 11.2 | 11.2 |

Fig.12

DIGITALLY MEASURING SCOPES USING A HIGH RESOLUTION ENCODER

CONTINUATION APPLICATION INFORMATION

This application is a continuation of U.S. patent application Ser. No. 08/502,984, filed Jul. 17, 1995, now U.S. Pat. No. 5,801,762, which is a continuation-in-part of U.S. patent application Ser. No. 08/365,636, filed Dec. 28, 1994, now U.S. Pat. No. 5,573,492.

BACKGROUND INFORMATION

The present invention concerns an arrangement, which includes a scope, such as a rigid borescope, a flexible fiberscope, or a videoscope for example, for accurately measuring observed objects, object details, and object defects. The arrangement of the present invention is more accurate than known systems, yet is simple to use.

Scopes, such as flexible videoscopes and fiberscopes have been used to observe the interior of the body during diagnostic procedures or surgery. Scopes, such as rigid borescopes, have been used to observe and inspect manufactured parts otherwise inaccessible to the eye. Although such scopes have an almost limitless number of applications, the following example illustrates their value.

A gas turbine engine includes a series of compressor and turbine blades, any one of which may become damaged. Although the first and last stage compressor/turbine blades of a gas turbine engine can be inspected directly, other intermediate stage compressor/turbine blades cannot be directly inspected. In the past, to inspect these intermediate stage compressor/turbine blades, the engine had to be disassembled until the intermediate stage compressor/turbine blade could be directly inspected. However, more recent gas turbine engines are provided with apertures (or borescope ports) provided at critical areas. These borescope ports permit the intermediate stage blades to be inspected using a borescope.

The borescope includes a long, thin, insertion tube having a lens system at its distal end and a viewing means at its proximal end. When the insertion tube of the borescope is inserted into a borescope port of the gas turbine engine, the lens system at its distal end relays an image of an otherwise inaccessible intermediate compressor/turbine blade to the viewing means at the proximal end. The focus of the image (in some models) can be adjusted by control knobs at the proximal end of the borescope. Hence, as illustrated by this example, a borescope permits an intermediate compressor/turbine blade of a gas turbine engine to be inspected without needing to disassemble the engine.

Besides being used to indirectly inspect parts which cannot be inspected directly, borescopes can also be used to measure the size of defects on the part. For example, U.S. Pat. No. 4,980,763 (hereinafter "the '763 patent") discusses a system for measuring objects viewed through a borescope. The system discussed in the '763 patent projects an auxiliary image, such as a shadow, onto the object being viewed. Changes in the position or size of the auxiliary image correspond to the distance between the object being viewed and the borescope. The image is displayed on a monitor having a magnification and object distance scale overlay on the screen. The size of the object on the screen is measured with vernier calipers, or electronically with cursors. This size is then divided by the magnification which is determined by observing where the auxiliary image falls on the magnification overlay. Unfortunately, the system discussed in the '763 patent requires a user to manually determine the magnification factor based on the position of the auxiliary image on the display screen.

U.S. Pat. No. 4,207,594 (hereinafter "the '594 patent") discusses a system in which the dimensions of a defect are determined based upon a manually entered field-of-view value and a ratio of second crosshairs, arranged at edges of a defect image, to first crosshairs, arranged at edges of the field of view. Unfortunately, the system discussed in the '594 patent requires probe penetration values to be manually read from a scale on the probe barrel for determining the field-of-view. Since such scales do not have fine gradations and since they must be manually read, errors are introduced.

U.S. Pat. No. 4,820,043 (hereinafter "the '043 patent") discusses a technoscope for determining the length of a defect. The technoscope includes a graduated scale which is displaceable in a direction transverse to the endoscope axis. The graduated scale is mechanically coupled with a detector which produces an electrical signal based on the transverse displacement of the graduated scale. The distance to the defect is determined by (i) observing the object image at a first terminal position of a fixed stroke Z of the endoscope, (ii) noting the intercept of the object image on the graduated scale, (iii) axially displacing the endoscope by the fixed stroke Z, and (iv) transversely displacing the graduated scale until the defect image intercepts it at the same point as before the axial displacement. A calculator uses the electrical signal from the detector and a known focal length of endoscope to determine the object distance. The size of the defect can be similarly determined. The technoscope of the '043 patent also includes a swing prism with a detector for determining its angular position.

Unfortunately, the scope of the '043 patent requires that the focal length of the endoscope be known ahead of time and requires two measurements. Moreover, since the distance between the two measurements must be fixed, the scope must be fixed with respect to the object during the two measurements. Furthermore, limitations in the gradations of the graduated scale limits the accuracy of the readings. Also, by manually reading the intercept point of the defect on the graduated scale, errors are introduced.

U.S. Pat. No. 4,702,229 (hereinafter "the '229 patent") discusses a technoscope for measuring an object. The technoscope includes an inner shaft which is axially displaceable with respect to an outer shaft. A measuring scale is provided in the inner shaft. The measurement of the object is determined by (i) placing an edge of the object image on the measuring scale, (ii) fixing the technoscope with respect to the object, (iii) axially displacing the inner shaft by a fixed distance, and (iv) observing how many scaler divisions the object image moved on the measurement scale. The object size is determined based on a known system focal length, the length of the displacement, and the number of scales moved by the object. The '229 patent is similar to the '043 patent except that with the '043 patent, the graduate scale is transversely repositioned such that the object intercepts it at the same point and the transverse position is determined with a mechanical detector. Therefore, the device of the '229 patent suffers the same drawbacks as the '043 patent, namely, (i) the focal length of the technoscope must be known, (ii) two measurements are needed, during which the technoscope must be fixed with respect to the object, (iii) limitations in the gradations of the measurement scale introduces errors, and (iv) the measurement scale must be manually read.

Known devices also use a magnification scale ring arranged adjacent to a focusing control ring having an indicator RV, for determining the magnification of the scope. Based on the position of the indicator of the focusing control ring with respect to the magnification scale, the magnification of the scope at that object distance is determined. Unfortunately, similar to the probe penetration knob in the system discussed in the '594 patent, such devices require magnification values to be manually read from a scale on the magnification barrel. Since such scales do not have fine gradations and since the magnification values must be manually read, errors are introduced. Even if the scale had fine markings, its diameter would have to be huge to have thousands of distinct "markings."

When such a scope is equipped with a graticule and a diopter focus control, this known device can also be used to determine the size of a viewed object. A graticule is a scale etched into a surface of a transparent glass plate included in the optical system. The diopter focus control is used to focus the graticule scale. An object is then focused by means of the focus control. Based on the number of graticules covered by the object image and based on the magnification level, the object size is determined. Unfortunately, the graticule scale is manually read which introduces errors. Manually reading the number of graticules covered by the object image also fatigues the user's eye. Moreover, since the number of markings on the graticule is limited, the accuracy is also limited. Furthermore, this method is inaccurate because the eye will accommodate an "out of focus" focus barrel position.

U.S. Pat. No. 4,558,691 (hereinafter "the '691 patent") discloses an endoscope in which an actual size of an observed object, a magnification of the scope, and an object distance can be determined based on a positional relationship between an indicating index and a stationary reference index. The indicating index is formed on a glass plate which moves up and down, perpendicular to the optical axis, as the lens barrel of the optical system moves back and forth along the optical axis. Unfortunately, as with the devices discussed above, the indicating index included in the device described in the '691 patent does not have fine gradations and must be manually read. This not only permits errors to be introduced, but also fatigues the eye of a user.

Japanese Patent Publication No. 5-288988 (hereinafter "the '988 publication") discusses the use of an encoder for determining changes in the magnification of a zoom lens system. However, this system is to be used for viewing objects at a fixed distance. That is, the encoder in the '988 publication determines changes in magnification of the scope but cannot determine the initial magnification of the scope and cannot determine object distance.

In view of the above described problems with existing scope measurement systems, a system for automatically measuring objects, with high resolution, is needed.

SUMMARY OF THE INVENTION

The present invention fulfills the above mentioned need by providing an arrangement including a scope having a focusing mechanism to which a high resolution encoder is coupled. The encoder sends a signal, corresponding to the position of the focusing mechanism, to a processor. The image from the scope is also sent to the processor. A processor executed program correlates the encoder signal to object size and/or magnification.

The encoder may be either a relative encoder or an absolute encoder, and may encode optically, electrically, and/or magnetically. However, in a preferred embodiment of the system of the present invention, the encoder is a relative, optical, encoder.

In a first embodiment of the present invention, the scope is a swing prism rigid borescope which allows the user to change the scope's direction of view from the scope body. The encoder is preferably a rotational optical encoder. The image from the scope is preferably sent to the video processor via a camera mounted to an eyepiece. In an embodiment of the system of the present invention using a relational encoder, the relational encoder increments and decrements an initial count based on adjustments of the focusing device. The initial count is set when the focusing device is placed in a predetermined home position.

In a second embodiment of the present invention, the scope is a flexible focusing fiberscope having a focusing lens system at a distal end and a focusing control at a proximal end. The focusing control at the proximal end actuates at least one lens of the focusing lens system at the distal end by means of a control cable or by means of a fine pitch flexible screw. The encoder may be a linear encoder located at the distal end for measuring the linear movement of the at least one lens of the focusing lens system, or it may be an encoder located at the proximal end for measuring a movement of the focusing control. In a third embodiment, the scope is a flexible video fiberscope having a focusing lens system at the distal end and a focusing control at the proximal end.

Optical encoders may include rotational encoders or linear encoders. The rotation encoders include an encoder disk, a light source and a detection device. The encoder disk has apertures, or reflective and non-reflective regions, arranged around its circumference, and is mechanically coupled with the focusing device such that it rotates when the focusing device is adjusted. The light source directs light towards a first side of the encoder disk. When an encoder disk having apertures is used, the detection device is arranged on a second side of the encoder disk, and generates a pulse when light from the light source passes through an aperture of the encoder disk. On the other hand, if an encoder disk with reflecting and non-reflecting regions is used, the detection device is arranged on the first side of the encoder disk and generates a pulse when light from the light source is reflected by the encoder disk. A linear encoder is similar to the disk encoder except it has a strip having a plurality of spaced apertures or a plurality of reflecting and non-reflecting regions, and is mechanically coupled with the focusing device such that it is linearly translated when the focusing device is adjusted.

The present invention provides a system for determining a dimension of a detail. The system at least includes an optical scope and a processor, and may also include a video camera, a display device, and a detail marking device. The optical scope produces an image of the detail and includes a focusing device and an encoder. Borescopes and fiberscopes also include a viewer. The focusing device adjusts a focal position of the image of the detail. With borescopes and fiberscopes, the viewer passes the image of the detail to a plane outside of the optical scope. With videoscopes, a video signal is provided. The encoder provides a focus position signal based a position of the focusing device.

The video camera produces a video signal of the detail from the image of the detail. In borescopes and fiberscopes, the video camera is optically coupled with the viewer of the scope, while in videoscopes, the video camera is internally mounted. The display device displays the detail based on the video signal of the detail. The detail marking device permits at least two markers, each having a coordinate value, to be arranged on the display of the detail on the display device. The processor converts the focus position signal from the encoder into an object distance signal and then into a magnification signal. The processor also determines the dimension of the detail based on the coordinate values of the at least two markers and based on the magnification signal.

In a preferred embodiment of the system of the present invention, the optical scope is a swing prism rigid borescope. The optical scope may also be a fiberscope or videoscope.

In a preferred embodiment of the system of the present invention, the video camera includes a charge coupled device which converts the image of the detail into the video signal of the detail. Further, in the preferred embodiment of the system of the present invention, the processor includes a first converter, such as a formula or a look-up table, for converting the focus position signal into an object distance signal, and a second converter, such as a formula or look-up table, for converting the object distance signal from the first converter into a magnification signal. In the preferred embodiment, the processor also includes a size processor for producing the dimension of the detail based on the magnification signal from the second converter and based on the coordinate values of the at least two markers.

In a preferred embodiment of the present invention, the optical scope includes a distal lens system, a focusing lens, a focus controller, and an encoder. If the optical scope is a borescope or fiberscope, it also includes a viewer. The distal lens system produces an image of a detail within its field-of-view. If the optical scope is a borescope or fiberscope, the viewer passes an image of the detail produced by the lens system to a plane outside of the scope. The focusing lens is located between the distal lens system and the viewer and can be linearly translated along its optical axis thereby permitting a focal position of the image to be adjusted. The focus controller linearly translates the focusing lens along its optical axis, whereby different positions of the focus controller correspond to different positions of the focusing lens. If the optical scope is a videoscope, a video camera, such as a CCD for example, converts an image to a video signal at the distal end. The focusing control actuates at least one lens in a lens system at the distal end. The encoder produces signals corresponding to the different positions of the focusing lens being translated or of the focus controller.

In an alternative embodiment of the present invention, the scope automatically focuses the image onto the video camera. In this embodiment, a stepper motor can actuate at least one lens of the focusing lens system. Alternatively, a user may make processor guided manual focusing adjustments. The user positions a cursor upon the video image of the detail to be measured. Alternatively, known methods of pattern detection could be used. A number of samples of windows (i.e., a predetermined number of pixels around the area of interest) are taken with the at least one lens of the focusing lens system at different positions. The at least one lens is translated by the stepper motor. The sampled window with the maximum contrast, as determined by a known method, is considered to be the most in focus. If there is more than one maximum contrast, the processor can choose either (i) the near focus side position having a maximum contrast, (ii) the far focus side position having a maximum contrast, or (iii) the average focus position of the maximum contrasts. This choice is predetermined. While any of the three choices can be used, it must be used consistently and can be the basis for system calibration.

In a preferred embodiment of the present invention, an optical distortion, based on an eccentricity of the image with respect to the focusing lens system, is corrected by the video processor. The eccentricity is determined based on the location of the image on the video camera and/or on the video monitor.

BRIEF DESCRIPTION OF THE DRAWINGS

FIGS. 9a through 9d are timing diagrams of outputs of the rotational encoder illustrated in FIG. 8.

FIG. 12 is a look-up table for determining object distance from the count produced by an exemplary encoder.

DETAILED DESCRIPTION

The following is a description of an exemplary embodiment of the present invention which employs a rotational encoder with a borescope. This example is not intended to limit the scope of the invention to rigid borescopes or to rotational encoders. Instead, the scope of the invention is defined by the claims which follow the detailed description.

Figure 1:
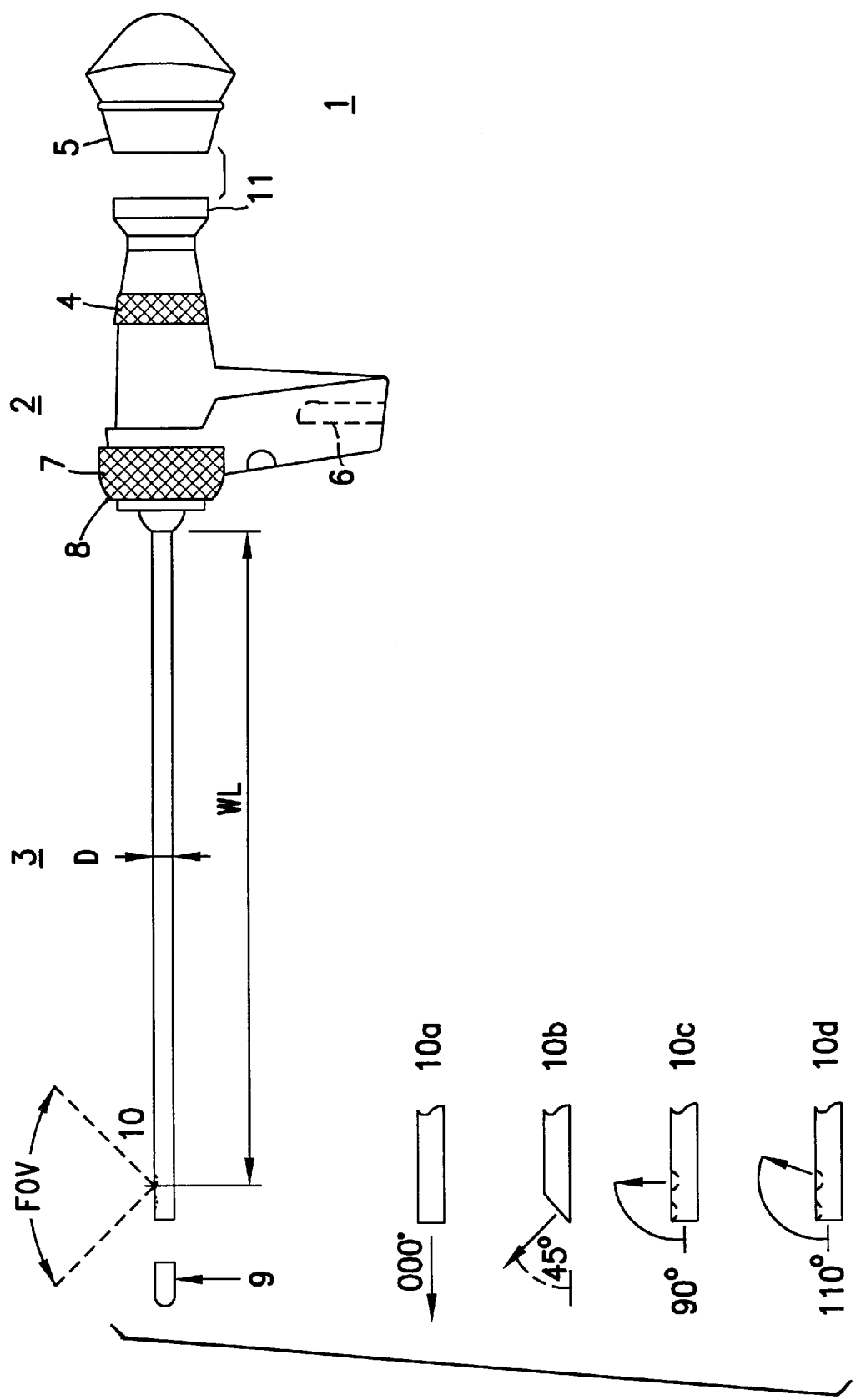
FIG. 1 is a side view illustration of a rigid borescope.

FIG. 1 is a side view illustration of a rigid borescope 1. The borescope 1 includes a body 2 and a long, thin arm (or insertion tube) 3. The insertion tube 3 is connected, at a proximal end, to the body 2, has an insertion length WL, and includes a lens system 10 at its distal end. The lens system 10 has a field-of-view defined by the angle FOV. As is illustrated in the partial side views of the insertion tube 3, different lens systems 10a through 10d have different directions of view. The distal end of the insertion tube 3 includes a cap 9 for protecting the insertion tube 3 from mechanical shocks resulting from inadvertent collisions. In a preferred embodiment of the present invention, the rigid borescope includes a swing prism, i.e., a prism which can be pivoted. The direction of view of such a swing prism can be adjusted from 45° to 120°. A sensor may be used to determine the angular position of the prism. Any angular prism position deviating from 90° introduces optical errors. These optical errors can be compensated for based on the sensor output.

Figure 10:
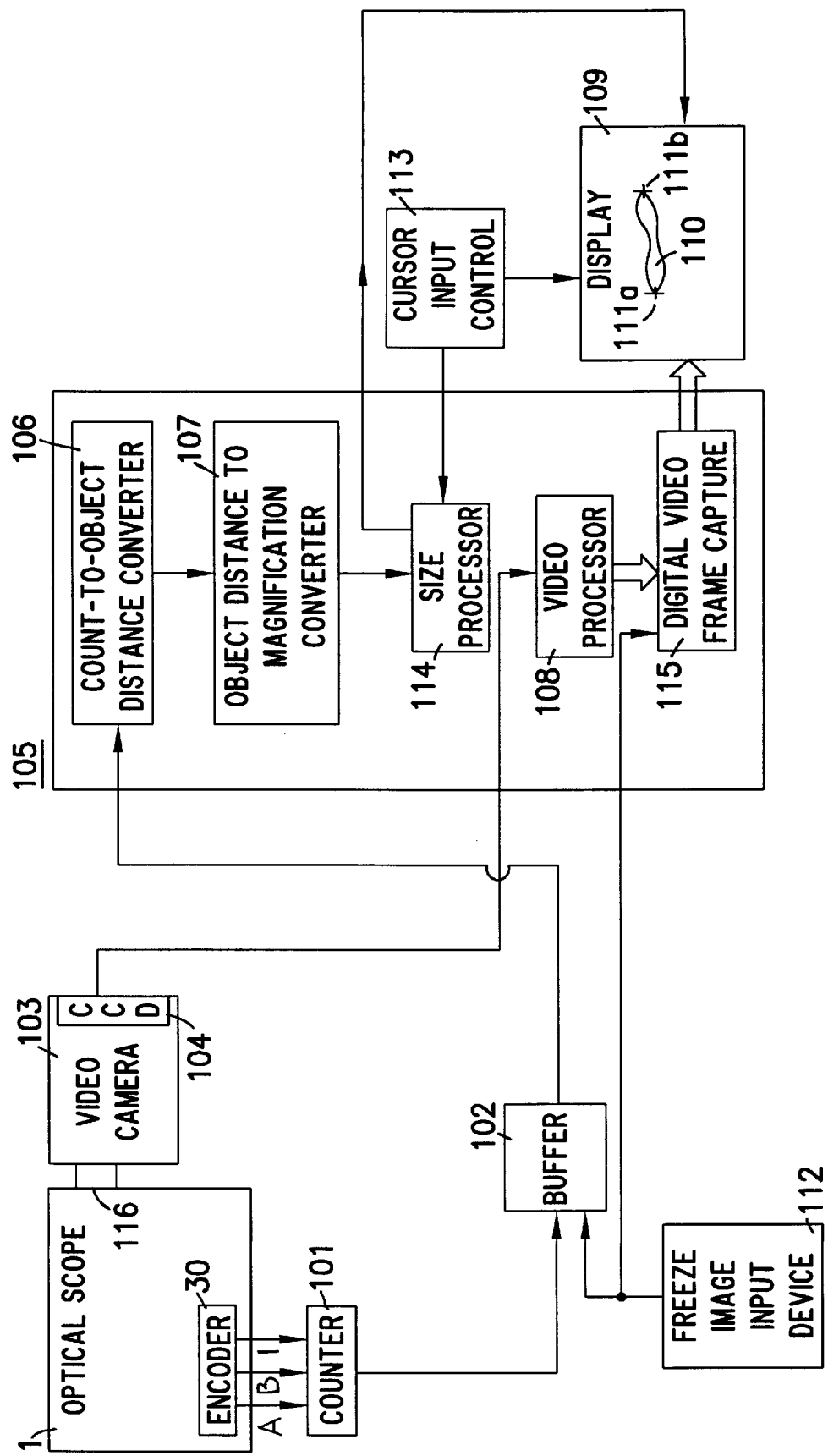
FIG. 10 is a functional block diagram of the system of the present invention.

The body 2 of the borescope 1 includes an orbital scan control 8, a focus control 4, a viewing means 11, and a light guide connector 6. The orbital scan control 8 is used for rotating the insertion tube 3 for capturing different views. The angular orientation of the insertion tube 3 is indicated with an orbital scan direction indicator 7. The focus control 4 permits the image gathered by the lens system 10 to be focused at the viewing means 11. The light guide connection 6 permits a light source (not shown) to be coupled with the borescope. The light from the light source may be carried by a fiber optic bundle, for example, to the distal end of the insertion tube 3 to illuminate objects within the field-of-view of the lens system 10. The viewing means 11 provides the image captured by the lens system 10. An eyecup 5 may be connected to the viewing means 11 for direct viewing. Alternatively, as illustrated in FIG. 10, a video camera 103 may be mounted to the viewing means by means of a viewing means-to-camera adaptor 116. The video camera 103 may transmit a video signal to a video processor 108.

A "focusing borescope" is a borescope with adjustable focus which produces a sharp image at a range of object distances. The narrow field-of-view (e.g. FOV=20 degrees) results in a shallow depth-of-field (DOF). As a consequence, with focusing borescopes, positions of the focus barrel correspond to object distances. Therefore, the focus barrel can be calibrated and used as a range finder. Since the log of the scope magnification and the log of the object distance have a linear relationship, the actual size of an observed object can also be determined.

Figure 2:
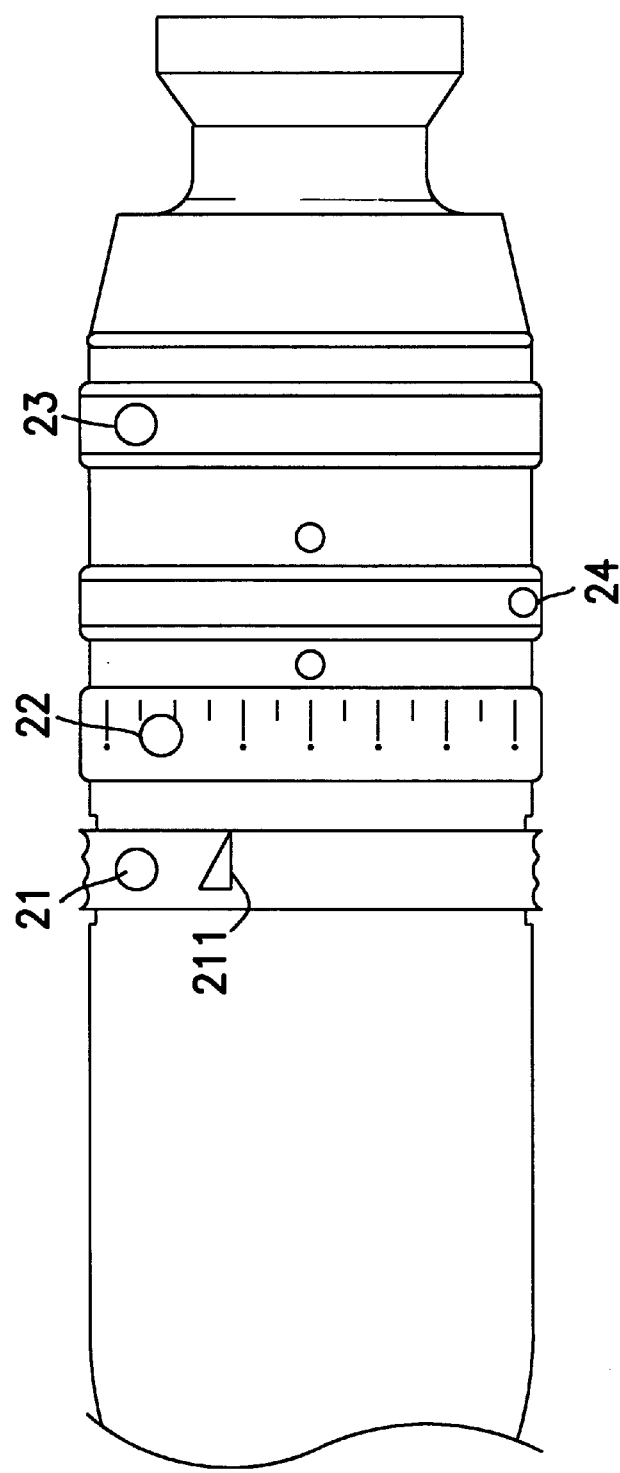
FIG. 2 is an illustration of a marked focus barrel used in known measuring scopes.

FIG. 2 is a marked focus barrel used in known measuring scopes, such as a focusing borescope for example. Such a marked focus barrel can be provided on the body 2 of the borescope 1 of FIG. 1 for example. The focus barrel of FIG. 2 includes a magnification scale 22, a diopter focus control 23, a graticule orientation control 24 and a focusing control 21 having an indicator 211. When the observed image is focused, the position of the indicator 211 of the focusing control 21 with respect to the magnification scale is used to determine the magnification of the image. As mentioned above, the log of the object distance is linearly related to the log of the scope magnification. Therefore, once the magnification of the image is determined, the object distance can be derived. Furthermore, as discussed in the Background of the Invention above, when the graticule (i.e., a scale etched into a surface of a coverglass included in the optic system) is focused with the diopter focus control 23, the size of the object being viewed can be determined based on the number of graticules occupied by the image of the object and based on the magnification of the scope.

Unfortunately, a number of error sources are introduced when using a scope with a marked focus barrel to determine the object distance, i.e., as a range finder. First, the resolution of the magnification value reading is limited by the gradations of the magnification scale. Also, there is a very practical limit to the number of graticule markings which limits the accuracy. Second, the magnification scale 22 and the number of graticules covered by the focused image must be manually read by a user. Third, manual calculations and confusing multiple step procedures introduce the possibility of human errors. Furthermore, the poor "ease of use" of scope measuring systems employing marked focus barrels and the experience of eye fatigue when using such scopes has limited their acceptability. More importantly however, is that the eye will accommodate slightly "out of focus" images. Furthermore, differences in the eyesights of different users will lead to different magnifications needed to focus the image. That is, users having different eyesights will result it different focus positions for the object being viewed.

Figure 3:
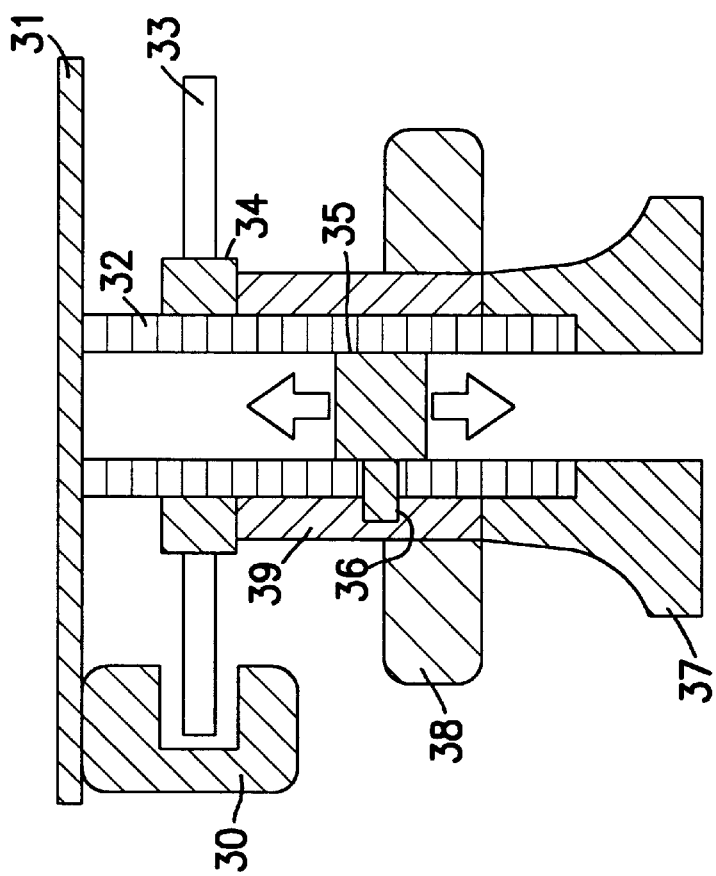
FIG. 3 is a cross-sectional side view of an ocular position rotational encoder to be used with the system of the present invention.
Figure 4:
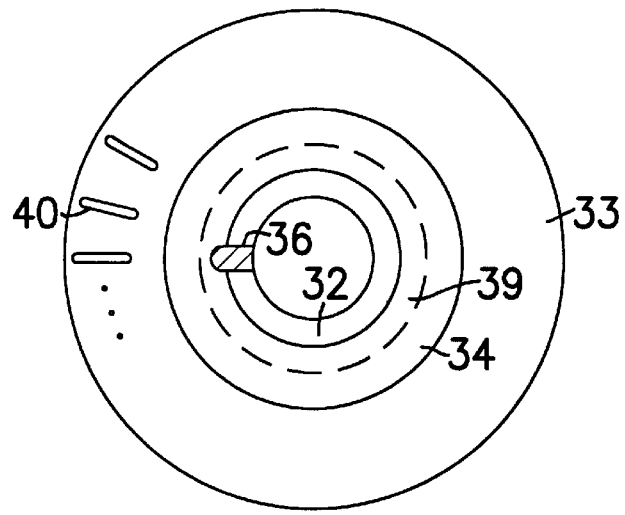
FIG. 4 is a plan view of the ocular position rotational encoder shown in FIG. 3.

FIG. 3 is a cross-sectional side view, and FIG. 4 is a partial plan view, of an ocular position rotational encoder which can be used in the scope measurement system of the present invention. The ocular rotational encoder includes an encoder pickup 30 (described in more detail with reference to FIG. 8), an encoder mounting plate 31, a borescope chassis 32, an encoder disk 33, an encoder disk hub 34, a carrier with an ocular lens 35, a ocular position pin 36, a viewing means 37, a focusing knob 38, and a focusing barrel 39.

The ocular position rotational encoder can be mounted to a rigid borescope by means of the mounting plate 31. The viewing means 37 is an eyepiece. However, as illustrated in FIG. 10, in the preferred embodiment of the present invention, a video camera 103 is mounted to the viewing means 37 with a camera adaptor 116. The video camera 103 transmits a video signal to a video processor 108 which displays the captured image 110 on a display monitor 109. This arrangement permits the image captured to be more accurately focused than would be possible with a human eye at the viewing means 37 because the video camera 103 includes an imaging means, such as a charge coupled device (CCD) 104, which is maintained at a fixed distance from the viewing means 37. Accordingly, the video camera 103 provides a "hard plane of focus" which is advantageous when compared with the different focus positions resulting from different users having different eyesights as discussed above and resulting from the eye's ability to accommodate slightly "out-of-focus" images.

When the focusing knob 38 is rotated about the optical axis, the ocular lens carrier 35 moves up or down as indicated by the arrows. By viewing the image on the display monitor, the focusing knob 38 can be used to precisely focus the image transmitted through the ocular lens held in the carrier 35. This is done as follows.

Figures 5, 6:
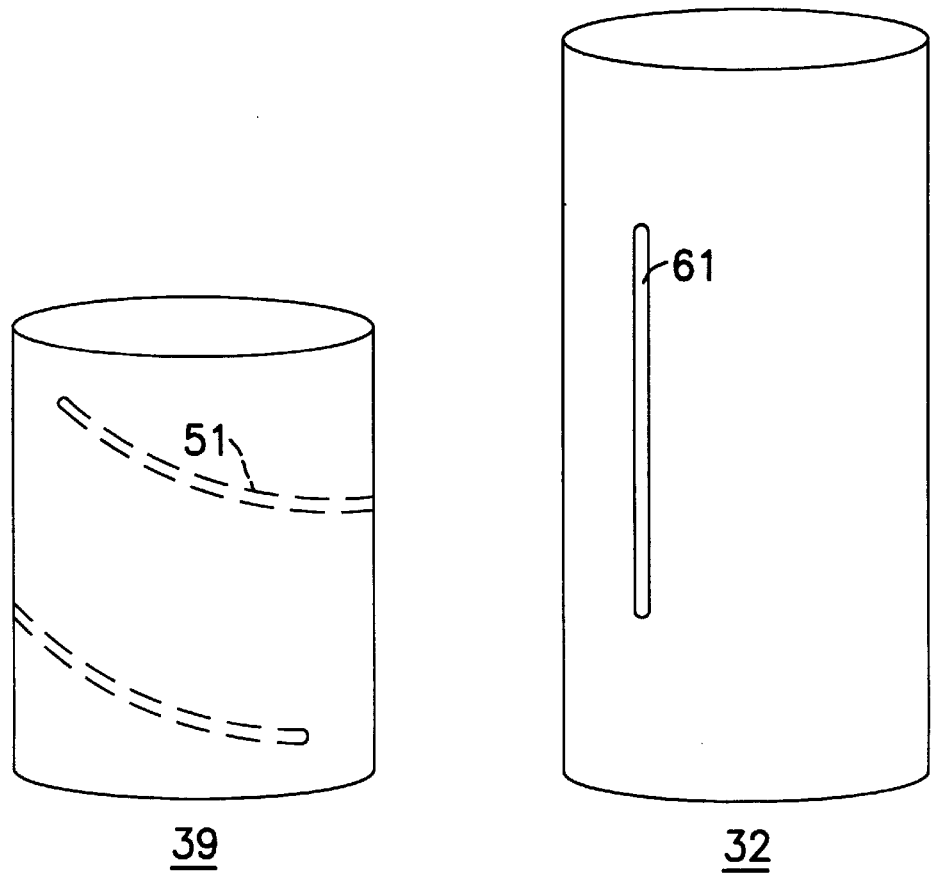
FIG. 5 is a perspective view illustrating a focus barrel having a spiral groove.
FIG. 6 is a perspective view illustrating a borescope chassis having a longitudinal slot.

The focusing knob 38 is mechanically coupled with the focusing barrel 39. In a preferred embodiment of the present invention, the focusing knob 38 is directly attached to the focusing barrel 39. As shown in FIG. 5, the focusing barrel 39 is cylindrical and has a spiral groove 51 cut into its inner surface. The ocular position pin 36 fits into the spiral groove 51. The inner surface of the focusing barrel 39 has a slightly larger diameter that the outer surface of the borescope chassis 32 thereby permitting the focusing barrel 39 to rotate about the borescope chassis 32. As shown in FIG. 6, the borescope chassis 32 has a longitudinal slot 61 through which the ocular position pin 36 projects. Accordingly, when the focusing knob 38 is rotated, the directly connected focusing barrel 39 also rotates about the borescope chassis 32. The spiral groove 51 on the inside surface of the focusing barrel 39 causes the ocular positioning pin 36 to ride up or down in the longitudinal slot 61 of the borescope chassis 32. Since the ocular positioning pin 36 is attached to the ocular lens carrier 35, the ocular lens can be moved up and down by rotating the focusing knob 38.

Figure 7A:
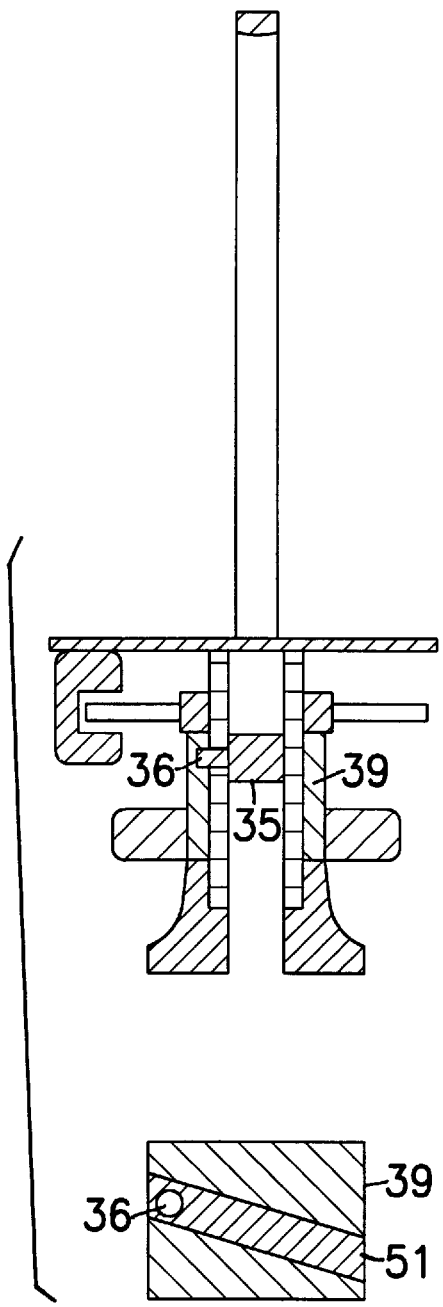
FIGS. 7a and 7b are cross-sectional side views of the ocular rotational encoder of FIG. 3 illustrating the difference in the positions of the elements of the encoder when viewing relatively distant objects and relatively close objects.
Figure 7B:
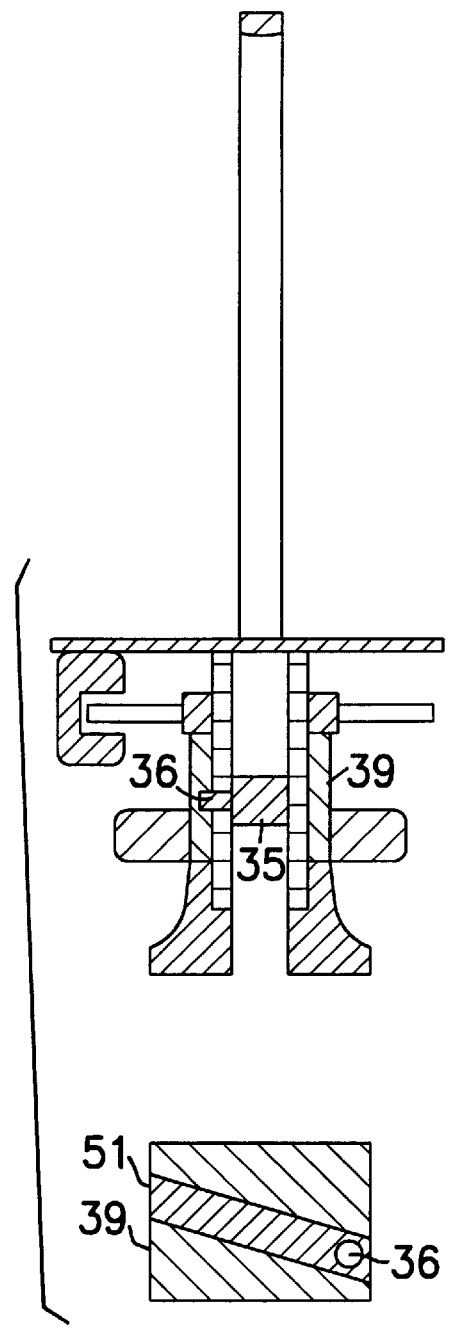

FIGS. 7a and 7b illustrate the relative positions of the ocular lens carrier 35 and of the ocular positioning pin 36 within the groove 51 on the inside surface of the focusing barrel 39, for an object relatively far from the borescope and for an object relatively close to the borescope, respectively. As illustrated in FIG. 7a, when the object distance is relatively large, the ocular lens carrier 35 is positioned far from the viewing means 37 and the ocular positioning pin 36 is located high in the spiral groove 51 on the inside surface of the focusing barrel 39. On the other hand, as illustrated in FIG. 7b, when the object distance is relatively small, the ocular lens carrier 35 is positioned close to the viewing means 37 and the ocular positioning pin 36 is located low in the spiral groove 51 on the inside surface of the focusing barrel 39.

As illustrated in FIG. 3, the focusing barrel 39 is also mechanically coupled with and preferably directly connected to, the disk hub 34 of the encoder disk 33. In a preferred embodiment of the present invention, as shown in FIG. 4, the encoder disk 33 has a number of slots or holes 40 (only three of which are shown for clarity) arranged around the encoder disk 33, spaced in equal angular increments. The encoder pick up 30, described in detail with reference to FIG. 8, determines the angular rotation of the encoder disk 33 by counting pulses received at the pickup 30.

The optical encoder which produces pulses corresponding to changes in the focal position, is a so-called "relational encoder". That is, an initial condition (i.e., an initial count) must be determined before the count is incremented or decremented. This initial condition is determined by locating the focal position to a predetermined "home" position for which the count is known or reset by the electronics, typically to zero. The known or reset count is then incremented and/or decremented when the focal position is moved from the "home" position. The "home" focal position is preferably located at at least one of the two extreme focal positions. Alternatively, a home position can be determined with an "indexing channel" as described below.

As an alternative to such "relational encoders," which increment and/or decrement a known count when the focal position is moved from a predetermined position, an "absolute encoder," which includes information about its absolute angular (or linear) position may be used.

Figure 8:
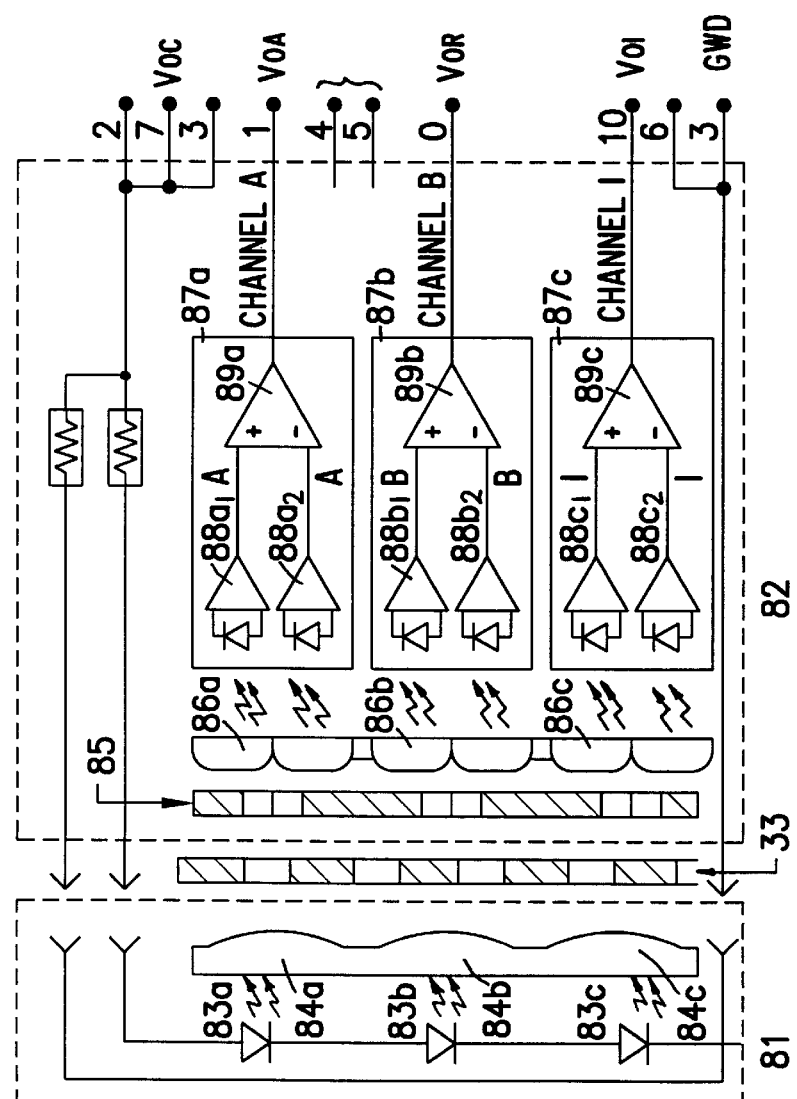
FIG. 8 is a schematic diagram of an emitter end plate, a code wheel, and an encoder body of a rotational encoder that can be used in the system of the present invention.

FIG. 8 is a schematic diagram of the encoder optical pick-up 30. The encoder optical pick-up 30 includes an emitter end plate 81 arranged adjacent to a first surface of the encoder disk 33 and an encoder body 82 arranged adjacent to a second surface of the encoder disk 33.

The encoder end plate 81 includes a series of light emitting diodes 83a through 83c for emitting light which is collimated by lenses 84a through 84c, respectively. These collimated light beams are directed towards the first surface of the encoder disk 33.

The encoder body 82 includes a phase plate 85, lens pairs 86a through 86c, and detection elements 87a through 87c for three (or two in an alternative embodiment) channels. Each of the channels 87a through 87c includes an integrated circuit having two photodiodes each having its own amplifier 88a through 88c. The amplifiers $88a_1$ through $88c_1$ are electrically coupled with a non-inverting input of comparators 89a through 89c, respectively, while the amplifiers $88a_2$ through $88c_2$ are electrically coupled with an inverting input of the comparators 89a through 89c, respectively.

The collimated light beams from lenses 84a through 84c must pass through a slit 40 in the encoder disk 33 and through an opening in the phase plate 85 to reach lens pairs 86a through 86c, respectively. The apertures in the phase plate 85 are positioned such that, for each photo-diode/amplifier pair 88a through 88c, a light period on one detector always corresponds to a dark period on the other. Accordingly, the output state of the comparators 89a through 89c changes when the difference of the two photo currents produced by the photo-diode/amplifier pairs 88a through 88c, respectively, changes sign.

Figure 9D:
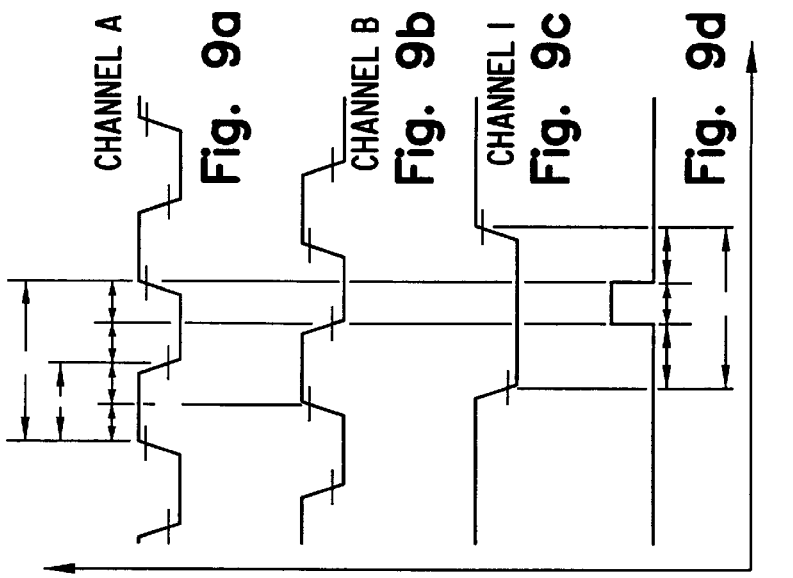

The phase plate 85 is also arranged so that the channel 87a is 90 degrees out of phase (i.e., in quadrature) with the channel 87b as is shown in the timing diagram of FIGS. 9a and 9b. This phase difference permits the direction of rotation to be determined by observing which channel is the leading waveform.

The channel 87c is an optional channel for performing an indexing function. Specifically, the channel 87c generates an index pulse for each rotation of the encoder wheel 33. This indexing channel can be used to define a "home" focal position having a known count, thereby providing an initial condition, i.e., an initial count, for this "relational" encoder.

FIG. 10 is a functional block diagram of the system of the present invention. An image captured by the borescope 1 is provided to a video camera 103 which is coupled with the viewing means 37 of the borescope 1 via a viewing means-to-camera adaptor 116. The video camera 103 includes an imaging device 104, such as a charge-coupled device (CCD) for example, for converting the optical signal to an analog video signal. The analog video signal is supplied to a video processor 108. The video processor 108 provides a video signal of the object to a video display monitor 109 via a digital video frame capturing device 115. The focusing knob 38 is adjusted until an image of the object 110 being observed appears in focus on the video display monitor 109. For objects oriented at an angle to the plane of the optical system of the scope, multiple points or regions of the object can be separately focused.

While the focusing knob 38 is being adjusted, the encoder 30 generates pulses corresponding to the angular rotation of the focusing knob 38. The encoder 30 transmits the pulses of channels 87a, 87b, and 87c to a counter 101. The counter 101 increments or decrements the count, depending upon whether the focusing knob 38 is being rotated clockwise or counter-clockwise, thereby forming a digital count value. An initial count is generated when the focus position is at "home" position as discussed above. The digital count value is stored in a buffer 102.

When the object being observed 110 appears in focus on the video display monitor 109, the user actuates a switch 112, such as a key of a keypad, to "freeze" the image. When the switch 112 is actuated, the digital count stored in the buffer 102 is read out and provided as an input to a count-to-object distance converter 106, and the video frame stored in the digital video frame capture 115 is read out and provided to the video display monitor 109. If multiple points or regions of an angled object are separately focused as provided above, the counts corresponding to the separate focus positions are averaged. In a further embodiment of the present invention, described more fully below, multiple points of a feature, such as a ding, can be separately focused and the measured point distances used to determine the depth (or height) of the feature or of parts of the feature.

The count-to-object distance converter 106 can be implemented as a predetermined formula for converting the digital count to an object distance. For example:

$$\log x = a(\log y)^2 - b (\log y) + c$$

wherein
x=object distance
y=encoder count
a,b,c=constants

Alternatively, the object distance can be determined from the count by means of a look up table including empirically determined data. FIG. 12 shows an example of such a look up table. If a look up table is used for converting the digital count to an object distance, an interpolation routine is preferably also used for determining object distances when the digital count falls between count values listed in the look up table.

Figure 11:
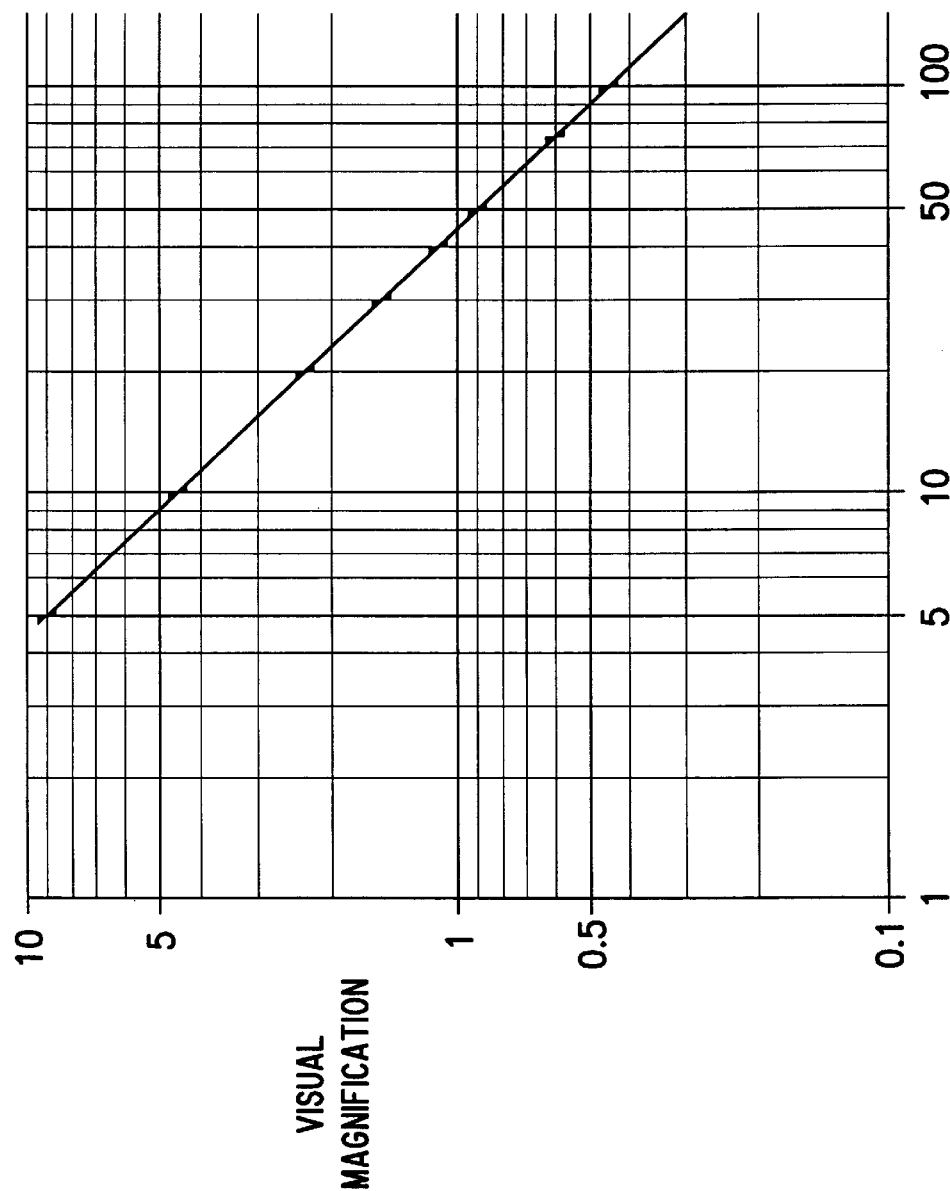
FIG. 11 is a graph illustrating the relationship between magnification and object distance for an exemplary borescope.

The object distance determined by the count-to-object distance converter 106 is provided as an input to an object distance-to-magnification converter 107. Similar to the count-to-object distance converter 106, the object distance-to-magnification converter 107 can be implemented as a predetermined formula for converting the object distance to a magnification value. Alternatively, the magnification value can be determined from the object distance by means of a look up table and an optional interpolator. As the graph shown in FIG. 11 illustrates, a linear relationship exists between the log of the magnification and the log of the object distance.

The system of the present invention also can automatically compensate for changes in the magnification from system to system due to differences in the video cameras (such as CCDs for example) and due to differences in the coupling between the eyepiece and the video camera. This automatic compensation eliminates the need to calibrate the magnification for each scope or system. The system of the present invention can also compensate for optical distortions due to image eccentricity. All optical systems distort. The main component of optical distortion for scopes results from images that do not pass through the center point of the lenses of the lens system. Specifically, an optical distortion is a function of the radial distance from the center of the lens to the point at which the image passes, i.e., the optical distortion is greater when the image passes through the edges of the lens than when the image passes through the center of the lens.

Figure 16A:
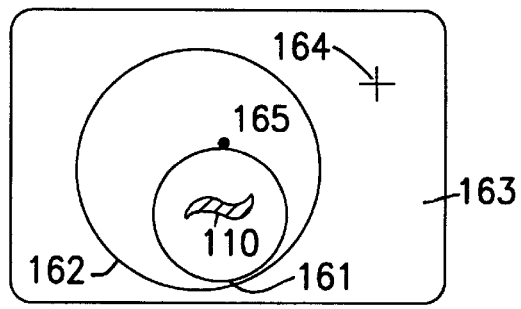
FIGS. 16a and 16b are video display screens for illustrating a process for determining magnification and radial distortion errors.
Figure 16B:
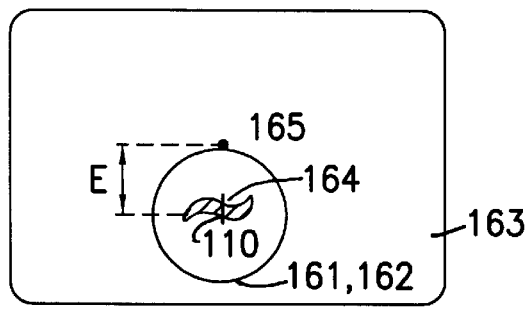
Figure 17:
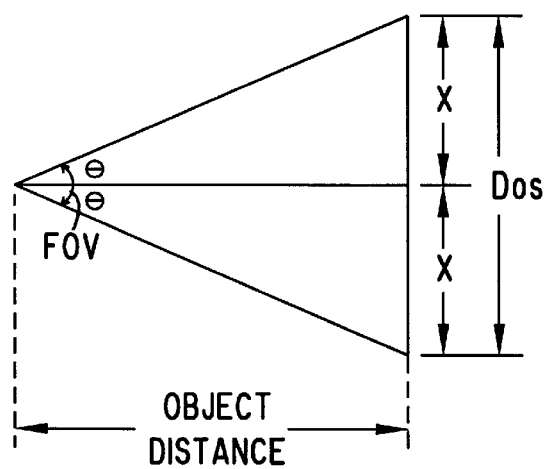
FIGS. 17 is a diagram which illustrates how magnifications are determined.

The system of the present invention automatically compensates for variations in magnification and for optical distortion as follows. FIG. 16a illustrates a screen of the display 109 showing the image of the defect 110. Since the actual image does not fill on the entire area of an imaging device (such as a CCD 104 for example) of the video camera 103, the scope image 161 does not fill the entire screen of the display 109. The size of the scope image 161 depends, at least in part, on the optical coupling of the image to the imaging device. A user can move and adjust the diameter of the circle 162 with an input device, such as the cursor input control 113, for example. The user moves and adjusts the circle 162 such that it coincides with the scope image 161 on the display. (See FIG. 16b). A processor, such as the size processor 114, compensates the magnification of the optical scope 1—video camera 103 combination based on the diameter of the circle 162. FIG. 17 is a diagram which illustrates the magnification compensation. Once the object distance (OD) is determined, the actual size of the diameter of the optical scope ($D_{OS}$) can be determined since the field of view (FOV=2θ) is known. Specifically $D_{OS}=2X=2$ [OD (tanθ)]. The magnification is then determined based on the ratio of the diameter of the circle 162 (when it coincides with the scope image 161) over $D_{OS}$.

FIG. 16a also illustrates a crosshair 164 which can be moved by a user with an input device, such as the cursor input control 113. As shown in FIG. 16b, the user can position the crosshair 164 at the center of the scope image 161 so that an eccentricity "E" from the center 165 of the display can be determined. A processor, such as the size processor 114 for example, can compensate for optical distortions based on the eccentricity "E".

The magnification compensation and the optical distortion compensation may be separately provided. However, if both are provided, the present invention preferably combines the crosshair 164 to coincide with the center of the circle 162 so that the image size and eccentricity can be determined based on a single user input. Alternatively, a processor executed program can determine the size of the scope image 161 and the eccentricity "E" automatically without requiring a user input. The optical scope may also include a non-volatile memory for communicating stored calibration information with other components of the system.

Referring back to FIG. 10, after a user actuates the freeze image switch 112, the user manipulates a cursor control input device 113, such as a keypad, a trackball, or a joystick, for example, to position at least two crosshairs 111a and 111b at ends of the object 110 being displayed. The coordinate positions of the crosshairs 111a and 111b, as well as the magnification factor, are provided as inputs to a size processor 114 which computes the length or size of the object 110 being displayed. Alternatively, a graticule (or reticle) provided in the optical scope can be used for providing scaled image information to the user. This scaled image information can be manually input into the size processor 114. Alternatively, a micro adjustable reticle can be used for marking and can be coupled with an encoder for providing direct inputs to the processor.

The display 109 can also optionally display the current object distance. As will be described more fully below, displaying the current, in-focus, object distance is useful for making depth and height measurements.

It should be evident from the above description that various combinations of the count-to-object distance converter 106, object distance-to-magnification converter 107 and size processor 114 are readily possible. For instance, the formulas or look up tables used to implement the count-to-object distance converter 106 and the object distance-to-magnification converter 107 can be implemented with one formula or look up table which uses the focus count from the buffer 102 as an input and provides the magnification value as an output. Similarly, the object distance-to-magnification converter 107 can be combined with the size processor 114 so that the object distance value from the count-to-object distance converter 106 can be used directly by the combined block (107/114) in determining the size of the object 110.

Figure 13:
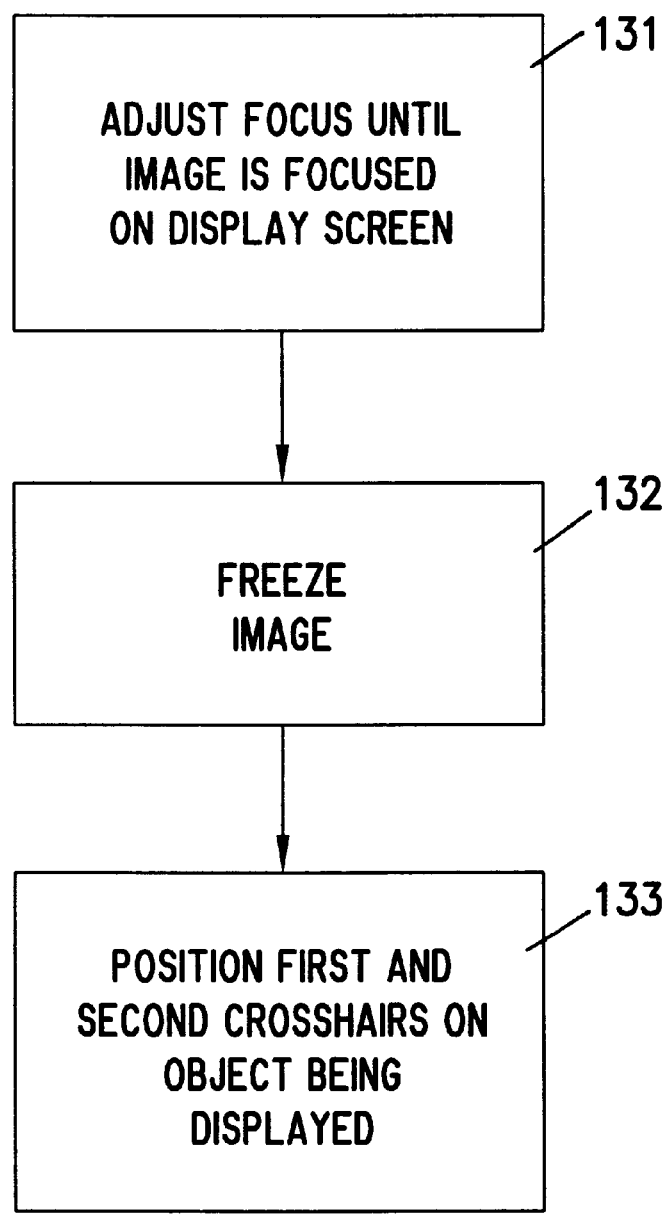
FIG. 13 is a flow diagram of a process for using the system of the present invention.

Operating the system of the present invention is almost fool-proof. Moreover, the system of the present invention reduces eye fatigue. As illustrated in the flow diagram of FIG. 13, the user is only required to execute three simple steps. First, the user must adjust the focus until the image on the display screen is focused as shown in step 131. Next, as shown in step 132, the user freezes the focused image. Finally, the user positions first and second crosshairs on the object being displayed as shown in step 133. Moreover, in the automatically focusing system described below, the user only has to perform step 133. Accordingly, a user is only required to execute three (or one) simple steps. This eliminates many errors that could otherwise be introduced by the user.

The above is an exemplary embodiment of the system of the present invention. One skilled in the art can modify the particular components suggested without departing from the scope of the invention recited in the claims. For example, a linear optical encoder for providing the position of the ocular positioning pin 36 can be used in place of the encoder disk 33 and its optical pickup 30. Such a linear encoder could be a plastic or metal strip, having equally spaced slits on it, and being mechanically coupled with the ocular positioning pin 36. An optical sensor can be used to count light and dark regions as the plastic or metal strip is moved with respect to it. Instead of slots, reflective and non-reflective regions can be used.

Furthermore, an electrical sensor, such as a rheostat, for example, or a magnetic sensor, such as a hall sensor for example, can be used to determine the position of the ocular lens. However, optical encoders are preferred because they provide high resolution in a relatively small package.

Similarly, the focusing barrel 39 can be mechanically coupled to the encoder disk hub 34 by gears instead of being directly connected. Also, instead of providing an encoder disk 33 with slits 40, a reflective encoder disk with pits can be used. Similarly, instead of incrementing and/or decrementing a count of slits (a relational encoder), the encoder disk can include coded angular position information (an absolute encoder).

Figure 14A:
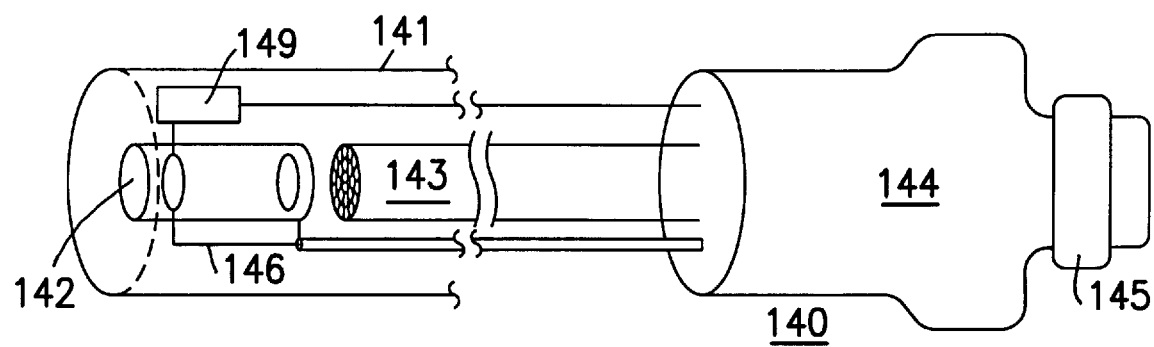
FIG. 14a is a schematic illustrating an objective fiberscope having a distally mounted encoder and having a proximal focusing cable to mechanically link a focus control with a focusing lens system.
Figure 14B:
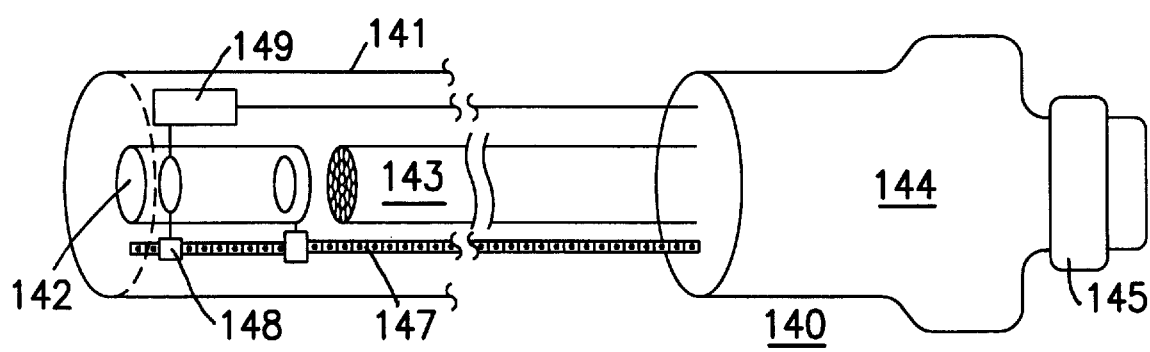
FIG. 14b is a schematic illustrating an objective fiberscope having a distally mounted encoder and having a flexible fine pitch screw and a fine pitch nut for mechanically linking a proximal focus control with a focusing lens system.
Figure 14C:
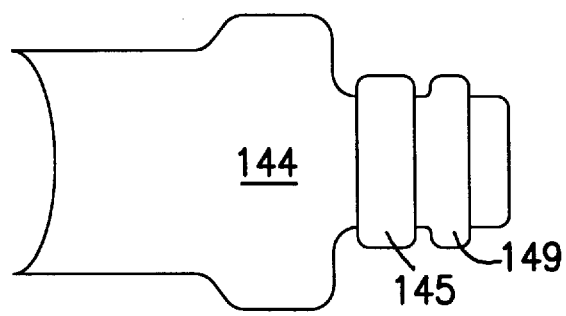
FIG. 14c is an alternative embodiment of FIGS. 14a and 14b in which a proximally mounted encoder is used instead of a distally mounted encoder.

A fiberscope or videoscope may also be used instead of a rigid borescope. As shown in FIG. 14a, the fiberscope 140 includes a flexible insertion tube 141 having a focusing lens system 142 at its distal end. A coherent fiber bundle 143 carries the image to the proximal end of the insertion tube where a lens system (not shown) provides an image to a viewer. Alternatively, the focusing lens system 142 can be provided at the proximal end of the coherent fiber bundle 143. The proximal end of the fiberscope 140 includes a scope body 144 with a focus controller 145. The focus controller 145 can linearly translate a lens of the focusing lens system 142 by means of a control cable 146 as shown in FIG. 14a or by means of a fine pitch flexible screw 147 and nut 148 as shown in FIG. 14b. In the alternative embodiment having the focusing lens system 142 at the proximal end of the coherent fiber bundle 143, the focus controller 145 can be more directly coupled with the at least one lens. As shown in FIG. 14c, the encoder 149 may be located at the proximal end of the fiberscope 140 to encode the movement of the focus controller 145. However, as shown in FIGS. 14a and 14b, the encoder is preferably a linear encoder located at the distal end of the fiberscope 140 to encode the linear movement of the lens. Providing the encoder at the distal end eliminates mechanical position errors due to flexing or stretching in the focusing control cable 146 or backlash in the flexible screw 147.

Figure 15A:
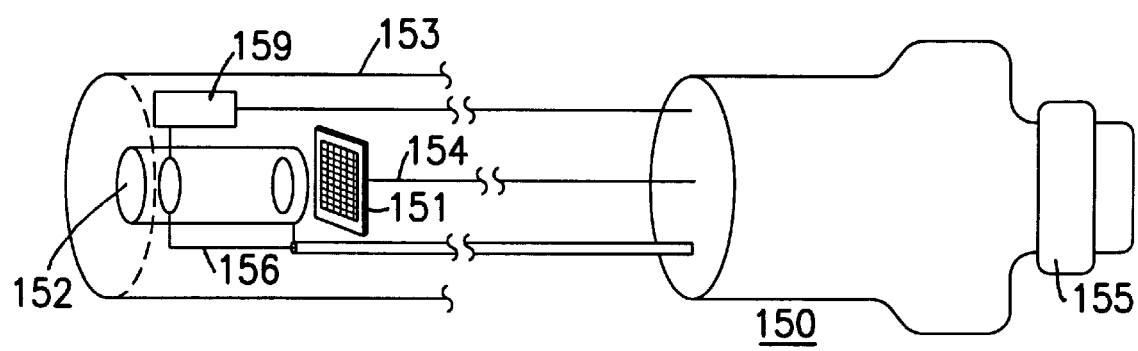
FIG. 15a is a schematic illustrating an objective videoscope having a distally mounted encoder and having a focusing cable to mechanically link a focus control with a proximal focusing lens system.
Figure 15B:
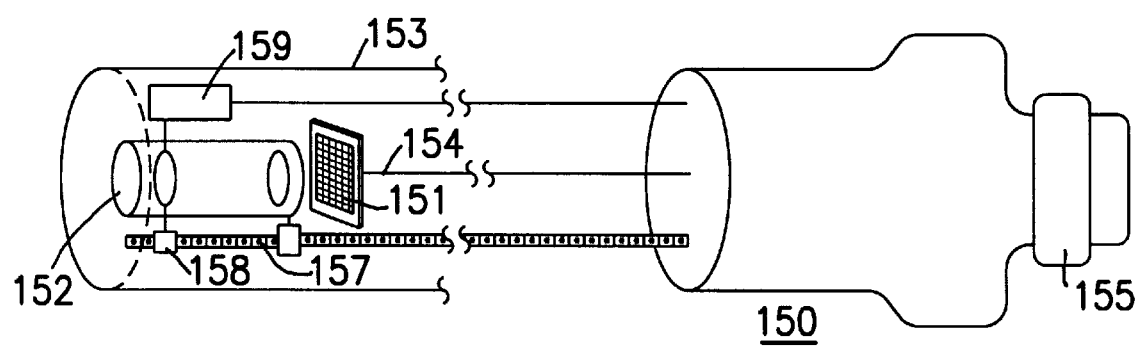
FIG. 15b is a schematic illustrating an objective videoscope having a distally mounted encoder and having a flexible fine pitch screw and a fine pitch nut for mechanically linking a proximal focus control with a focusing lens system.

As shown in FIGS. 15a and 15b, a videoscope 150 has a video camera 151, such as a CCD, adjacent to a focusing lens system 152 at the distal end of a flexible insertion tube 153. The video camera 151 converts the image to a video signal which is carried to the proximal end of the videoscope by means of a video signal cable 154. Accordingly, a viewer is not required in a videoscope.

Figure 15C:
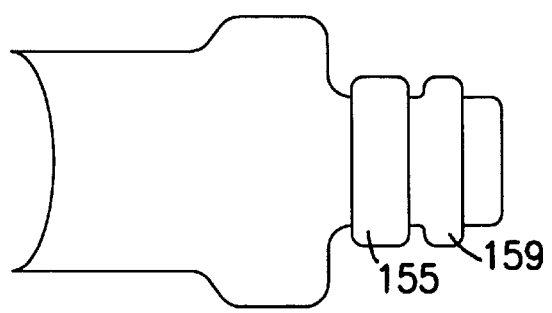
FIG. 15c is an alternative embodiment of FIGS. 15a and 15b in which a proximally mounted encoder is used instead of a distally mounted encoder.

As discussed above with reference to the fiberscope 140, a focus controller 155, located at the proximal end of the videoscope 150, can linearly translate a lens of the focusing lens system 152 by means of a focusing control cable 156 (See FIG. 15a.) or by means of a flexible screw 157 and nut 158 (See FIG. 15b.). Also, as discussed above with reference to the fiberscope 140, the encoder 159 may be located at the proximal end of the videoscope to encode the movement of the focus controller 155 (See FIG. 15c.) but is preferably a linear encoder 159 located at the distal end of the videoscope for encoding the linear movement of the lens (See FIGS. 15a and 15b.). In both the videoscope and fiberscope, if a mechanical means is used to couple the focusing control with the at least one lens, mechanical play in the mechanical means can be compensated for by a processor.

If a fiberscope 140 is used, the system is similar to the system of FIG. 10 which uses a borescope as the optical scope 1. However, if a videoscope 150 is used, the viewing means-to-camera adaptor 116, the externally mounted video camera 103 with CCD 104 are not needed since the videoscope 150 includes an internal video camera such as a CCD 151 for example.

In alternative embodiments of the scopes and systems of the present invention, an automatic focusing device can be used in addition to, or in place of, the focusing knob 38 of the borescope or the focusing controls 145 and 155 of the fiberscope 140 and videoscope 150, respectively.

Figure 19A:
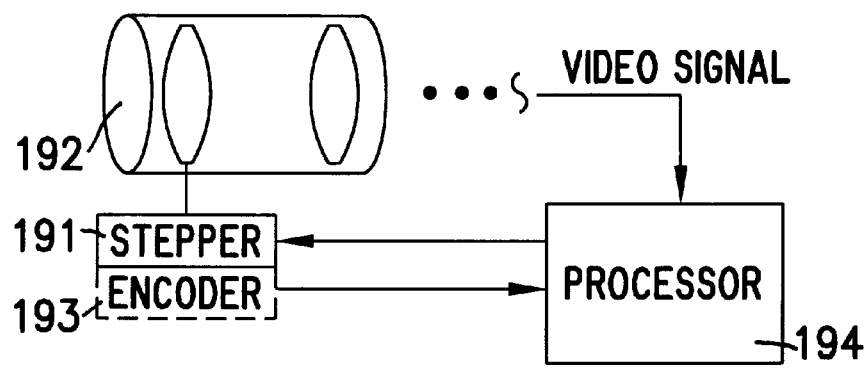
FIG. 19 is a schematic diagram illustrating additional elements used in an automatically focusing scope.
Figure 19B:
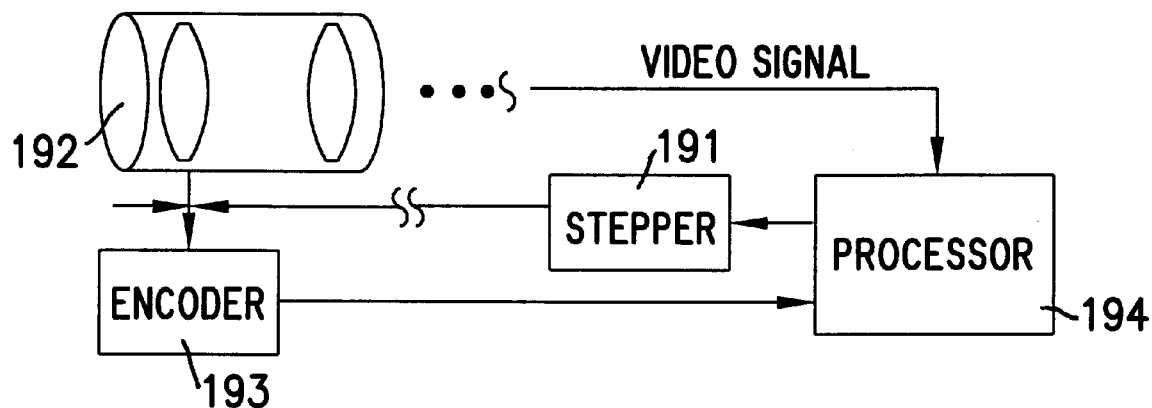

As shown in FIGS. 19a and 19b, a stepper motor 191 is mechanically coupled with at least one lens of a focusing lens system 192, by the means of a focus control cable or a fine pitch flexible screw for example. An optional encoder 193 may also be mechanically coupled with the stepper motor 191 (See FIG. 19a.) or with the at least one lens of the focusing lens system 192 (See FIG. 19b.).

Figure 18:
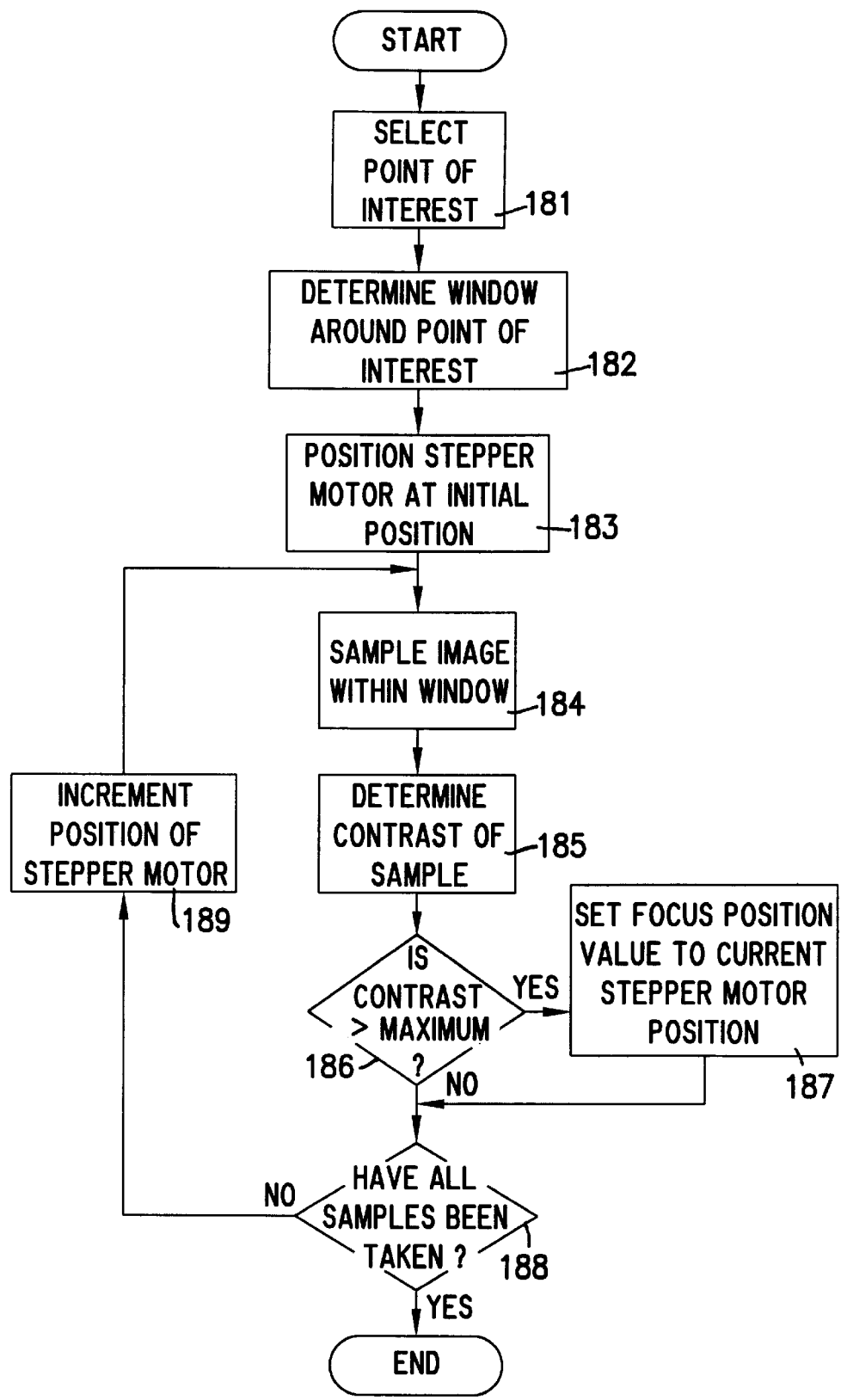
FIG. 18 is a flowchart of an automatic focusing procedure of the present invention.

The object image is automatically focused with a processor 194 executed program. FIG. 18 is a flow chart illustrating the program for automatic focus. At step 181, the user selects a point of interest via an input device, such as the cursor input control 113 for example. Alternatively, the processor 194 can select a point of interest using a known defect detection algorithm. Next, a window is defined around the point of interest at step 182. The window may be predetermined or may be defined by the user. The window is preferably a rectangle but may be another geometric shape. For example, the processor 194 can define a 10 pixel by 10 pixel box centered around the point of interest. In a preferred embodiment, the size of the window is limited decrease processing time.

In steps 183 and 184, the stepper motor is placed in an initial position and the image within the window is sampled. In step 185, the contrast of the sampled image is determined in a known way. For example, the average of the magnitude of the differences in brightness between adjacent pixels can be determined. The higher the average, the higher the image contrast. Alternatively, a Fast Fourier Transform (FFT) of the image can be determined. The higher frequency, the more complex the image and the higher the contrast.

Step 186 determines whether the contrast determined in Step 185 is a maximum. Since the maximum contrast value corresponds to the "best focus," a focus position value is related to the current stepper motor position in step 187 when the contrast is a maximum.

Steps 184 through 187 are repeated until a range of stepper motor positions is complete, as illustrated by steps 188 and 189. If a maximum contrast is determined at more than one stepper motor position, the best focus is selected from either (i) a maximum contrast position nearest to the focus size, (ii) a maximum contrast position farthest from the focus side, or (iii) an average of the maximum contrast positions. In an embodiment having automatic focusing and a defect detection process, a display is not required.

As can be inferred from FIG. 19a, it is possible to eliminate the encoder 193 and base the focus position on the number of steps executed by the stepper motor 191. This would be especially practical if a small stepper motor could be arranged at the distal end of the insertion tube. If however, the stepper motor 191 is located at the proximal end of the scope as in FIG. 19b, an encoder 193 is preferably included at the distal end of the insertion tube to eliminate any errors due to mechanical "play" in the mechanical coupling between the stepper motor 191 and the at least one lens of the focusing lens system 192. Alternatively, a user may make processor guided manual adjustments.

In a preferred embodiment of the present invention, a focus knob (or focusing controller) is used with the stepper motor in a "hybrid" focusing operation. A user first uses the focusing knob to coarsely focus the image. The stepper motor then performs a fine image focus under control of the processor as described with respect to FIG. 18. Such a "hybrid" operation is advantageous because the range of stepper positions at which the image is to be sampled and analyzed is decreased.

The system of the present invention can also be used to measure depth and height by determining the difference between the measured object distances of two points. For example, the depth of a round-bottomed ding in the surface of a turbine blade can be determined by 1) first focusing the device of the present invention on the surface of the blade and determining the object distance, 2) recording the measured object distance to the blade surface, 3) focusing on the bottom of the ding and determining the object distance, and 4) subtracting the recorded object distance to the blade surface from the object distance to the ding bottom, thereby yielding the depth of the ding.

The above-described procedure can be carried out manually using any of the embodiments of the present invention described thus far. For example, with the embodiment of FIG. 10, the user can note the object distances displayed on the display 109 for the two points of interest (i.e., the blade surface and the ding bottom) and subtract the two quantities to determine the depth of the ding.

The system of the present invention can provide various features to facilitate the depth/height measurement procedure. The embodiment of FIG. 10, for example, can be adapted to provide such features by modifying the software used to program the system. For example, once the user causes the system to focus on the first point, e.g., the blade surface, and has hit image freeze switch 112, the object distance, as determined by the count-to-object distance converter 106, is temporarily stored by the software in a register or memory location (not shown). When the user causes the system to focus on the second point, e.g., the ding bottom, and hits the image freeze switch 112, the system will subtract the stored object distance from the current object distance, as generated by the converter 106, and display the difference on the display 109.

Optionally, once the first point has been focused and measured, as the system is being re-focused and before the freeze switch 112 is pressed again, the system can display the current object distance, the stored object distance of the previously frozen image, and/or the difference between the two object distances. By updating and displaying, in real time, the current object distance and/or the difference between the current object distance and the stored object distance, the user can search for the lowest point (or highest point) of the feature whose depth (or height) is to be determined.

The procedure for determining the depth or height of a feature can be automated even further with the system of the present invention. For example, in one embodiment, once the user has aimed the scope at a feature whose depth or height is to be determined, the system can then automatically carry out the depth/height measurement procedure. Using the automatic focusing procedure described above, the system can focus on and determine the object distance of each of a predefined number of uniformly distributed points within a window of a predefined size surrounding the feature. Once all points within the window have been measured, the system then determines the minimum and maximum values of the plurality of object distances measured. The system then determines the difference between the minimum and maximum object distance values, which difference represents the depth or height of the feature.

It will be appreciated that when measuring the depth or height of a feature relative to a surrounding flat surface, the scope should preferably be oriented so that its optical axis is perpendicular to the surface. If this, however, is not the case, at least three points on the surface must be measured in order to identify the plane of the surface. Once the plane has been identified, the feature's depth or height relative to the plane can then be determined. Such a procedure can be carried out, for instance, with the embodiment of FIG. 10 with modified software. Using the cursor control, the user can define three points in the plane surrounding the feature of interest. The system of the present invention then automatically focuses on and determines the object distance for each of the three points. Using the cursor position information and the object distance calculated for each point, the system thereby has three-dimensional coordinates for each point. The system then uses those coordinates to determine the plane of the surface surrounding the feature of interest. When the user then positions the cursor on the displayed image of the feature, the system measures the object distance to the point defined by the cursor and calculates and displays the depth or height of that point on the feature relative to the plane surrounding the feature. The user can then iteratively position the cursor on the displayed image of the feature until he determines the maximum depth or height, or any intermediate depth or height of interest. This procedure can also be further automated, as discussed above, by programming the system to automatically focus and measure multiple points in a window surrounding a feature.

For applications which only call for the measurement of the depth or height of features, as opposed to their width, a simplification of the system of the present invention can be achieved by eliminating the determination of the magnification. In this case, only the object distance is required.

What is claimed is:

1. A system for determining a dimension of a feature, the system comprising:

a) an optical scope for gathering an image of the feature, the optical scope including i) a focusing device for adjusting a focal position of the image of the feature, ii) a device for detecting a position of the focusing device and for providing a focus position signal based on the position of the focusing device, and iii) an image-to-video converter for producing a video signal of the feature from the image of the feature having its focal position adjusted by the focusing device;

b) an image scaling device for providing a scaled image size; and c) a processor, the processor
  i) converting the focus position signal into at least one of an object distance signal and a magnification signal, and
  ii) determining the dimension of the feature based on the scaled image size and based on the at least one of the object distance signal and the magnification signal, wherein the dimension of the feature includes at least one of a depth and height of the feature.

2. The system of claim 1, wherein the processor includes:
  i) a converter for converting the focus position into an object distance signal; and
  ii) means for determining the dimension of the feature by determining the difference between a first object distance signal and a second object distance signal.

3. A system for determining a dimension of a feature, the system comprising:
  a) an optical scope for producing an image of the feature, the optical scope including
    i) a focusing device for adjusting a focal position of the image of the feature,
    ii) a viewer for passing the image of the feature to a plane outside of the optical scope, and
    iii) a device for detecting a position of the focusing device and for providing a focus position signal based on the position of the focusing device;
  b) a video camera optically coupled with the viewer of the optical scope and producing a video signal of the feature from the image of the feature;
  c) an image scaling device for providing a scaled image size; and
  d) a processor, the processor
    i) a converting the focus position signal into at least one of an object distance signal and a magnification signal, and
    ii) determining the dimension of the feature based on the scaled image size and based on the at least one of the object distance signal and the magnification signal, wherein the dimension of the feature includes at least one of a depth and height of the feature.

4. The system of claim 3, wherein the processor includes:
  i) a converter for converting the focus position into an object distance signal; and
  ii) means for determining the dimension of the feature by determining the difference between a first object distance signal and a second object distance signal.

5. A system for determining a dimension of a feature, the system comprising:
  a) an optical scope for gathering an image of the feature, the optical scope including
    i) a focusing device for adjusting a focal position of the image of the feature, and
    ii) a device for detecting a position of the focusing device and for providing a focus position signal based on the position of the focusing device;
  b) a processor, the processor
    i) converting the focus position signal into an object distance signal, and
    ii) determining a dimension of the feature based on the object distance signal.

6. The system of claim 5, wherein the dimension of the feature includes at least one of a depth and height of the feature.

7. The system of claim 6, wherein the processor includes:
  i) a converter for converting the focus position into an object distance signal; and
  ii) means for determining the dimension of the feature by determining the difference between a first object distance signal and a second object distance signal.

* * * * *